US011998336B2

(12) United States Patent
Gross et al.

(10) Patent No.: US 11,998,336 B2
(45) Date of Patent: *Jun. 4, 2024

(54) SYSTEMS AND METHODS FOR ASSESSING USER PHYSIOLOGY BASED ON EYE TRACKING DATA

(71) Applicant: RightEye, LLC, Bethesda, MD (US)

(72) Inventors: Adam Todd Gross, Potomac, MD (US); Melissa Hunfalvay, Silver Spring, MD (US)

(73) Assignee: RightEye, LLC, Bethesda, MD (US)

( * ) Notice: Subject to any disclaimer, the term of this patent is extended or adjusted under 35 U.S.C. 154(b) by 154 days.

This patent is subject to a terminal disclaimer.

(21) Appl. No.: 17/454,250

(22) Filed: Nov. 10, 2021

(65) Prior Publication Data

US 2022/0061724 A1 Mar. 3, 2022

Related U.S. Application Data

(63) Continuation of application No. 16/269,166, filed on Feb. 6, 2019, now Pat. No. 11,207,011.

(Continued)

(51) Int. Cl.
*A61B 5/16* (2006.01)
*A61B 3/113* (2006.01)
(Continued)

(52) U.S. Cl.
CPC .............. *A61B 5/163* (2017.08); *A61B 3/113* (2013.01); *G16H 50/30* (2018.01); *G16H 50/70* (2018.01); *A61B 3/0016* (2013.01); *G16H 50/20* (2018.01)

(58) Field of Classification Search
CPC ...... A61B 3/113; A61B 3/0008; A61B 3/0016; A61B 3/0025; A61B 3/0033;
(Continued)

(56) References Cited

U.S. PATENT DOCUMENTS 9,101,312 B2 8/2015 Waldorf et al.
9,265,416 B2 2/2016 Klin et al.
(Continued)

OTHER PUBLICATIONS

International Search Report and Written Opinion issued in International Application No. PCT/US2019/016849 dated Apr. 29, 2019 (16 pages).

(Continued)

*Primary Examiner* — David J. McCrosky
(74) *Attorney, Agent, or Firm* — Bookoff McAndrews, PLLC

(57) ABSTRACT

Systems and methods are disclosed for assessing user physiology via eye tracking data. One method includes determining a plurality of visual assessments; determining, for each assessment of the plurality of visual assessments, a data schema, where at least one data schema is associated with more than one assessment of the plurality of visual assessments; storing the determined data schema; receiving user eye tracking data associated with a selected visual assessment of the plurality of visual assessments; determining, of the stored data schema (a), a selected stored data schema associated with the selected visual assessment; categorizing the received eye tracking data based on the selected stored data schema; computing quantitative data based on the categorized data and data related to one or more individuals other than the user; generating a report of user physiological function based on the computed quantitative data; and outputting the report to a web portal.

20 Claims, 3 Drawing Sheets

Related U.S. Application Data

(60) Provisional application No. 62/654,513, filed on Apr. 8, 2018, provisional application No. 62/627,603, filed on Feb. 7, 2018.

(51) Int. Cl.
*G16H 50/20* (2018.01)
*G16H 50/30* (2018.01)
*G16H 50/70* (2018.01)
*A61B 3/00* (2006.01)

(58) Field of Classification Search
CPC ... A61B 3/0041; A61B 3/0058; A61B 3/0075; A61B 3/0091; A61B 3/032; A61B 5/168; A61B 3/024
See application file for complete search history.

(56) References Cited

U.S. PATENT DOCUMENTS

| | | |
|---|---|---|
| 9,730,582 B1 | 8/2017 | Stone et al. |
| 2018/0008141 A1 | 1/2018 | Krueger |
| 2018/0333092 A1 | 11/2018 | Roshan et al. |

OTHER PUBLICATIONS

"Web portal—Wikipedia", Jan. 28, 2018, Retrieved from the Internet: URL;https://en.wikipedia.org/w/index.php?title=web_portal&oldid=822771758 [retrieved on Apr. 4, 2019] (7 pages).

SYSTEMS AND METHODS FOR ASSESSING USER PHYSIOLOGY BASED ON EYE TRACKING DATA

RELATED APPLICATIONS

This application is a continuation of and claims the benefit of priority to U.S. patent application Ser. No. 16/269,166, filed on Feb. 6, 2019, which claims priority to U.S. Provisional Application No. 62/627,603 filed Feb. 7, 2018 and U.S. Provisional Application No. 62/654,513 filed Apr. 8, 2018, the entire disclosures of which are hereby incorporated herein by reference in their entireties.

TECHNICAL FIELD

Various embodiments of the present disclosure relate generally to evaluating, assessing, and improving human physiological performance using eye tracking data. More specifically, exemplary embodiments of the present disclosure relate to a cloud-based platform that processes eye tracking data to provide assessments and recommendations related to the user's physical or neurological function.

BACKGROUND

Visual assessments, consumer skill optimization, and medical evaluations are currently offered through disparate channels. Basic eye exams for common eye issues are available at optometrist sites and increasingly via mobile applications. Lifestyle-oriented mobile applications may also help consumers seeking to optimize their capabilities, in reading faster, becoming better athletes, elevating their performance at their jobs, etc. Further, medical facilities and schools are facing increasing demand for noninvasive, pre-emptive, and accurate medical tests, e.g., for attention-deficit/hyperactivity disorder, Parkinson's disease, depression, dementia, rehabilitation, etc. Current visual assessments address only basic, rudimentary eye issues (e.g., myopia), rather than the skills optimization sought by consumers or the medical evaluations sought by medical patients. Also, consumers seeking to optimize their abilities partake in assessments and exercises that differ from the tests that medical patients undergo.

Accordingly, a need exists for systems and methods for providing a range of assessments and training options (e.g., for skills optimization or medical treatment) via a single platform.

SUMMARY

According to certain embodiments, methods are disclosed for assessing user physiology via eye tracking data. One method includes determining a plurality of visual assessments; determining, for each assessment of the plurality of visual assessments, a data schema, where at least one data schema is associated with more than one assessment of the plurality of visual assessments; storing the determined data schema; receiving user eye tracking data associated with a selected visual assessment of the plurality of visual assessments; determining, of the stored data schema (a), a selected stored data schema associated with the selected visual assessment; categorizing the received eye tracking data based on the selected stored data schema; computing quantitative data based on the categorized data and data related to one or more individuals other than the user; generating a report of user physiological function based on the computed quantitative data; and outputting the report to a web portal.

According to certain embodiments, systems are disclosed for hosting one or more visual assessments. One system includes a data storage device storing instructions for assessing user physiology via eye tracking data; and a processor configured to execute the instructions to perform a method including: determining a plurality of visual assessments; determining, for each assessment of the plurality of visual assessments, a data schema, where at least one data schema is associated with more than one assessment of the plurality of visual assessments; storing the determined data schema; receiving user eye tracking data associated with a selected visual assessment of the plurality of visual assessments; determining, of the stored data schema (a), a selected stored data schema associated with the selected visual assessment; categorizing the received eye tracking data based on the selected stored data schema; computing quantitative data based on the categorized data and data related to one or more individuals other than the user; generating a report of user physiological function based on the computed quantitative data; and outputting the report to a web portal.

According to certain embodiments, a computer readable medium is disclosed storing instructions that, when executed by a computer, cause the computer to perform a method of assessing user physiology via eye tracking data, the method including determining a plurality of visual assessments; determining, for each assessment of the plurality of visual assessments, a data schema, where at least one data schema is associated with more than one assessment of the plurality of visual assessments; storing the determined data schema; receiving user eye tracking data associated with a selected visual assessment of the plurality of visual assessments; determining, of the stored data schema (a), a selected stored data schema associated with the selected visual assessment; categorizing the received eye tracking data based on the selected stored data schema; computing quantitative data based on the categorized data and data related to one or more individuals other than the user; generating a report of user physiological function based on the computed quantitative data; and outputting the report to a web portal.

Additional objects and advantages of the disclosed embodiments will be set forth in part in the description that follows, and in part will be apparent from the description, or may be learned by practice of the disclosed embodiments. The objects and advantages of the disclosed embodiments will be realized and attained by means of the elements and combinations particularly pointed out in the appended claims.

BRIEF DESCRIPTION OF THE DRAWINGS

The accompanying drawings, which are incorporated in and constitute a part of this specification, illustrate various exemplary embodiments and together with the description, serve to explain the principles of the disclosed embodiments.

DESCRIPTION OF THE EMBODIMENTS

Figure 1:
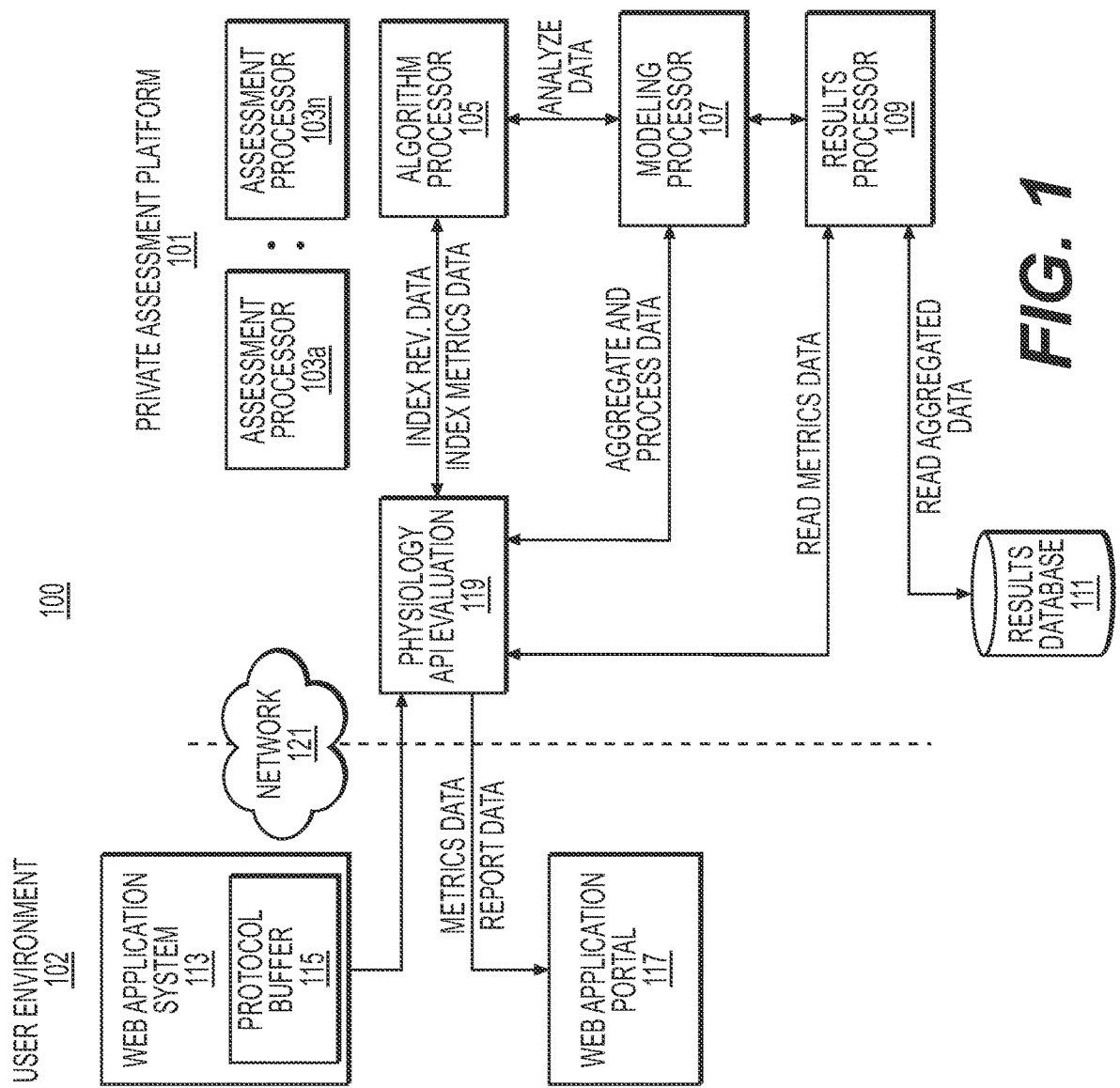
FIG. 1 is a block diagram of an exemplary physiological assessment system that uses eye tracking data, according to an exemplary embodiment of the present disclosure.

Reference will now be made in detail to the exemplary embodiments of the disclosure, examples of which are illustrated in the accompanying drawings. Wherever possible, the same reference numbers will be used throughout the drawings to refer to the same or like parts.

Although visual assessments are widely available, the visual assessments often evaluate only common eye issues. Recent consumer trends also emphasize optimization of capabilities (e.g., improved reading speed or comprehension, athletic ability, work performance, etc.) and noninvasive, preemptive medical tests. Currently, visual assessments, capability optimization services/apps, and medical testing all take place in separate settings, though disparate channels and providers. Accordingly, a need exists for systems and methods for providing a range of assessments and training options (e.g., for skills optimization or medical treatment) from a single source.

In particular, the disclosed systems and methods recognize that eye tracking data may provide visual assessments, skill optimization, and medical diagnostic testing and treatment. In view of the challenges outlined above, the present disclosure provides systems and methods for conducting and generating visual, skills-based, and medical assessments based on eye tracking data. Specifically, the disclosed systems and methods enable communication between various physiological assessment applications that generate and collect user eye-tracking data. The assessments may relate to different evaluation, training, or diagnostic purposes. For example, one assessment may relate to improving a user's athletic ability (e.g., training a tennis player to anticipate a movement) while another assessment may relate to diagnosing a neurological disorder. The disclosed systems and methods may provide a base of metrics computed from eye tracking data that may be common across the different assessments. In one embodiment, the communication may be provided via a hosting platform, as described in U.S. patent application Ser. No. 15/342,230 filed Nov. 3, 2016, the entire disclosure of which is hereby incorporated by reference in its entirety.

The disclosed assessments may include any evaluations of eye movement data, including assessments of a user's visual performance and/or assessments of a user's neurological state. Visual performance may encompass all measures of a user's vision, e.g., a user's visual ability (e.g., a static ability that may be predetermined by the user's genetic composition), a user's visual capacity (e.g., abilities of a user that may be flexible or abilities that may vary with practice, training, therapy, etc.), a user's visual status (e.g., a user's eye movement and neurological responses at a given point in time), a user's eye movement response as a result of a user's neurological function, etc. In other words, visual performance may refer to a user's eye movement being normal (e.g., associated with a usual, healthy individual), above normal (e.g., an expert, professional-level, or experienced athlete, vehicle driver, hunter, etc.), or impaired (e.g., due to injury or a neurological disorder). Exemplary neurological disorders may include, for instance, Parkinson's Disease, Autism, Attention Deficit Disorder, stroke, Cerebral Palsy, Multiple Sclerosis, Dementia, etc. A user's neurological state may encompass a user's neurological function at a given point in time, including a user's progression in gain or loss of neurological function related to eye movements and vision.

Turning now to the figures, FIG. 1 is a block diagram of an exemplary physiological assessment system 100 including a private cloud, backend environment (e.g., private assessment platform 101) and a user-facing, front-end environment (e.g., user environment 102). The private assessment platform 101 may comprise a cloud environment hosting multiple human physiological assessments relating to eye tracking data. In one embodiment, the assessment platform 101 may receive any eye movement data, e.g., data collected from any eye tracking device (e.g., via a web application system 113 to be discussed in further detail). The assessment platform 101 may further convert received eye movement data to a format usable by any visual assessment application hosted by the assessment platform 101. For one embodiment, the assessment platform 101 may analyze a set of foundational vision metrics, e.g., fixation stability, saccades, smooth pursuit, dynamic visual acuity, cardinal gaze position, reaction time, reading ability, etc.) to generate assessments of a user's physiology. In other words, the assessment platform 101 may collect and analyze foundational vision metrics to generate conclusions on a user's physiology.

Assessment platform 101 may host a plurality of assessment applications (e.g., assessment processors 103a-103n), an algorithm processor 105, a modeling processor 107, a results processor 109, and a results database 111. The assessment processors 103a-103n may have various configurations and be associated with one or more application programming interfaces (APIs), as described in U.S. patent application Ser. No. 15/342,230 filed Nov. 3, 2016, the entire disclosure of which is hereby incorporated by reference in its entirety. In one embodiment, each assessment may exist as a set of algorithms. The assessment platform 101 may integrate each set of algorithms of each of the hosted assessments into the foundational metrics of the platform 101, e.g., via algorithm processor 105. The foundational metrics may then be used to provide results for any assessments hosted on the assessment platform 101. In other words, the algorithm processor 105 of the assessment platform 101 may provide continuity between several visual assessments and their respective eye tracking collection mechanisms and calculations. The algorithm processor 105 may further evaluate user performance across multiple visual assessment applications and provide recommendations for the user to improve, maintain, or rehabilitate his or her visual performance. Additionally, the assessment platform 101 may leverage data and analyses from multiple visual assessment applications to improve user performance evaluations and recommendations, e.g., via modeling processor 107.

In one embodiment, algorithm processor 105 may determine a data schema for each assessment hosted by the assessment platform 101. The algorithm processor 105 may further categorize eye tracking data of user(s) based on the data schema. For example, algorithm processor 105 may index raw data according to the data schema. Raw eye tracking data may include x, y, and/or z coordinates and/or calibration data directly measured or provided by an eye tracker tracking a user's eye movement while taking an assessment. Alternately or in addition, algorithm processor 105 may further index and categorize metrics (e.g., computed quantitative data). In this way, the algorithm processor 105 may facilitate data discovery for evaluating a given user or for building diagnostic/expected metrics for each assessment. For example, for a selected assessment, algorithm processor 105 may access metrics categorized as being related to the assessment. The categorized metrics may then be used by modeling processor 107 to create "expected" or baseline metrics. Operations of the algorithm processor 105 may be observed and revised by support or IT personnel.

Categorized metrics may include categorical data that provides indications of a group to which collected raw data may belong. Categorized metrics provide a first step for further analysis (e.g., by modeling processor 107). For example, age data may provide place collected data in an age bracket, to later analyze whether age is a factor that influences results. The same is true for demographics data including gender, ethnicity, handedness etc. Other examples of categorical data may include notes (e.g. clinical observations, including whether a patient wore eye glasses), feature data (e.g., games, saccades, lights or stimuli being on or off, etc.), user identifying data (e.g., participant, company, or assessment identifier(s), etc.), HIPAA data (e.g., name, date of birth, gender, etc.), survey data including input data from third parties (e.g., entered by a patient/user or doctor, online survey services or websites, or backend assessment (e.g., assessment platform 101, trainer(s) and personnel), business analytics (data used to provide sales and customer success information on the customer usage, including medical codes), etc.

Categorical data may follow certain rules designated by the assessment platform 101 and/or component(s) of the web application system 113 (e.g., protocol buffer 115). The rules may provide a form of standardization. Standardizing data across the platform 101 may provide a known output understood by researchers, engineers, users, medical professionals, etc. Standardization may provide interpretation documentation that reduces questions from such parties, allowing the raw data and quantitative data (described in further detail below) to be better understood. Standardization may also reduce error in output and facilitate interpretation and cleaning of the data. Further, standardization in categorization of data may provide guidance to all parts of the platform 101, including guidance on testing to follow in evaluating the accuracy of assessments and guidance on computation of data for interpretation. Standardization performed by the assessment platform 101 and/or the web application system 113 may additionally include creating automated rules for consumption of data for interpretation. The automated rules may facilitate and speed data interpretation.

In one embodiment, algorithm processor 105 may use proprietary algorithms to compute metrics based on received raw eye tracking data. For example, one algorithm may include performing one or more steps including grouping samples collected during a presentation of stimuli (of an assessment). For instance, an assessment may show stimuli positioned at various degree points of a screen, and raw eye tracking data samples may be separated into groups according to the position of the stimuli presented. Alternately or in addition, an algorithm may include checking data quality or filtering out certain data samples. For instance, collected data may entail some loss of data samples. Data collection that fails to meet a certain quality (e.g., loss of samples being less than 10%) may trigger a prompt for a user to re-take an assessment. Exemplary filtering of data samples may include filtering out and removing gaze data of zero from the collected data.

Algorithm processor 105 may also be configured to calculate gaze points for each sample, e.g., sample of filtered and data quality-certified data. Gaze point calculation may include, for instance, averaging left eye and right eye gaze data to find gaze data for both eyes of the user taking the assessment. Alternately or in addition, algorithm processor 105 may determine locations of samples. For example, for each sample, algorithm processor 105 may determine the location of the sample in relation to the target band (within 9 mm), 1st error band (within 9-18 mm), 2nd error band (within 18-36 mm) on the left or right side of a screen displaying a selected assessment (of assessment processors 103), or outside of these bands on the left or right side of the screen.

Calculations of velocities may also be performed, e.g., finding the velocity associated with each sample using a distance/time calculation. Again, the samples used to calculate velocities may also be sample(s) of filtered and data quality-certified data. Algorithm processor 105 may also calculate fast and slow phase velocity for each stimulus. For example, for each sample during the stimuli presentations, if the eyes are within an error radius, and if the eyes move past the stimulus and perform a saccade to return to the target, the algorithm processor 105 may record the velocity as a fast phase movement. If eyes are moving toward the stimulus within the error radius and have not moved past the stimulus, algorithm processor 105 may note the eye movement as a slow phase. For each of the fast and slow phase velocities for each stimuli, algorithm processor 105 may then calculate the mean (or average) fast phase and slow phase velocity for each stimuli and the associated standard deviation (SD).

Using velocity and distance, and timing thresholding, algorithm processor 105 may also categorize sample(s) a saccade, smooth pursuit, or fixation. For example, samples with velocities greater than 30°/second may be marked as saccades. For samples that are not labeled as saccades, contiguous samples may be grouped together if they meet predetermined distance and timing thresholds. This grouping may be labeled as fixations. Remaining samples may be labeled as smooth pursuit. Saccade, smooth pursuit, and fixation percentages may be calculated based on the time each eye movement occurred over the time of analysis.

Algorithm processor 105 may also compute On Target, Predictive, and Latent Smooth Pursuit Percentage(s). For example, for each sample labeled as a smooth pursuit, that sample may be labeled as an on target smooth pursuit sample if the sample is within a predetermined distance threshold from the stimulus when the samples was recorded. Of the sampled eye tracking data that fall outside the distance threshold but within a given error radius, samples that are ahead of the stimulus at the time the sample was recorded may be labeled/categorized as predictive smooth pursuit samples, and samples behind the stimulus at the time the sample was recorded may be categorized as latent smooth pursuit samples. Samples outside of this error radius may not be considered to be tracking the stimulus and are therefore not considered in these metrics.

Algorithm processor 105 may also compute eye target velocity error by taking the difference of the sample's velocity with the stimuli's velocity, for each sample. The average across samples may be a user's target velocity error. Algorithm processor 105 may further compute synchronization. First, the instantaneous phase for the horizontal (x) and vertical (y) component of the eye tracking samples as well as the stimuli's coordinates during the assessment may be computed. Next, the phase difference between the eye and the stimuli may be computed. From this, the synchronization value can be determined by finding the intensity of the first Fourier mode.

Algorithm processor 105 may also be configured to determine scoring. For example, for each sample, algorithm processor 105 may determine the direction (left or right) moved and the furthest point the eyes made on that side, using computed location information. If the detected location of the eyes fall within a target region/band, a score may be assigned based on the region. If the location of the eye(s) fall in an error band, algorithm processor 105 may determine if the eye(s) moved passed the vertical midpoint of that band. If they did, the algorithm processor 105 may categorize the eye movement as an overshot. Otherwise, the eye movement may be categorized as an undershot. Eye locations that fall outside all of the target bands may be categorized as misses. Saccades may be categorized as the number of times the user traveled from one side of the assessment screen to the other. Fixations may be a category for any data showing stopping points, or anytime the user hit a target, error band, or missed a target.

The modeling processor 107 may provide computations based on the categorized eye tracking data. For example, modeling processor 107 may aggregate data received from multiple users to develop norms for each data schema, including determining data that characterizes expected, healthy, or normal conditions. Modeling processor 107 may develop norms by analyzing the categorized data. For instance, modeling processor 107 may select variable(s) for each assessment and employ various data analysis techniques, including feature reduction, supervised learning, outlier detection, object recognition, of a combination thereof. The modeling processor 107 may perform one or more data analysis operations for each assessment with supervision, or automatically. In one embodiment, the modeling processor 107 may produce calculated data. Calculated data may include qualitative data and quantitative data.

Qualitative data may be represented in numbers or described in words. Qualitative data may be received from surveys (asking people for feedback or health status) or clinical notes (made by healthcare or medical professionals). Quantitative data may include processed numerical data collected by the eye tracker and categorized by the platform 101. Quantitative data may be hierarchical in platform 101. Previously described raw data and categorical data may be considered quantitative data. The modeling processor 107 may further compute quantitative data using the raw data and categorical data. Exemplary computed quantitative data may include value(s) for metric(s) (e.g., smooth pursuit percentage), model data, model data, comparative data (e.g., percentiles, comparisons of gaze paths, functional bandwidth, etc.), indicators and scores (e.g. binocular scores), confidence data (e.g., reliability in computed metric(s), calibration for head movement, percentage of samples lost, data collection issues, etc.), normative data, age-based norms, skill level norms, etc.

Results processor 109 may compare a selected user's eye tracking data to the norms developed by modeling processor 107 and provide reports or results for the assessment taken by a user. At the same time, the eye tracking data may be used to compute or supplement the development of norms for other assessments. For example, assessment platform 101 may store eye tracking data from a user taking an assessment to improve her athletic ability, and the eye tracking data may be used to provide baseline data for an Alzheimer's assessment. In one embodiment, the results database 111 may store the processed results of multiple users and assessments in the data schema designated by the algorithm processor 105.

In generating assessments for a particular user, the results processor 109 may produce data visualizations from aggregated data and computed values of metrics. For example, results processor 109 may draw from prior, stored results relating to the particular user as well as prior users. The prior users may have taken the same assessment as the particular user, or different assessment(s). As long as the prior users' data is stored by the data schema, the modeling processor 107 may user the prior users' data to generate norms or expected results for a selected assessment that the particular user took, and the results processor 109 may evaluate the particular user using the generated norms. Results database 111 may aid in collective analysis of a plurality of users. Stored data from the results database 111 may be used to improve the data collection and/or analytics of platform 101. Results database 111 may include a database of formatted data and/or computed values of one or more metrics. Alternately or in addition, platform 101 may include a cache (not shown) including real-time or raw data.

The data of platform 101 may be viewed as falling into six levels of data that build on one another. Level 1 data may include raw eye tracking data (e.g., x, y, and z coordinates). Level 2 data may include filtered raw data. For example, raw data may be filtered to remove anomalies, e.g., high velocity reflections. Level 2 data may provide the basis for valid calculations. Level 1 and level 2 data may provide a foundation on which to build further calculations (e.g., regarding fixations, saccades, smooth pursuits, etc.) Level 3 data may include classified eye movement data. The classified data may identify oculomotor events. Level 4 data may then take the base calculations of oculomotor data and, using formulas (e.g., of algorithm processor 105), calculate groups of data or compute one or more values of metric(s). For example, for the metric of smooth pursuit, level 4 data may provide a percentage of time a user's gaze is in smooth pursuit. Level 5 data may use level 1, 2, and 3, data to make calculations across groups of individuals/users. For example, level 5 data may include a smooth pursuit percentage of a particular user compared to all other test-takers of an assessment. Level 5 metrics may comprise model data, including data for data mining, cleaning, or feature reduction for identifying an outcome, e.g., identification of far-sightedness or near-sightedness. Level 6 data may include metrics that permit interpretation of data for a particular user, e.g., actually identifying if the user is near-sighted or far-sighted. Level 6 data may allow the results processor 109 to provide results based on the user's assessment responses and the responses of population(s).

Physiology evaluation application programming interface (API) 119 may provide the interface between the backend private cloud environment 101 and a user-facing (front-end) user environment 102. API 119 may be associated with a storage service or database for raw eye tracking data received from a user taking an assessment. The database may store raw eye tracking data, filter the raw data, classify eye movement detected in the raw data, and store data schema that may map raw data to one or more metric(s). API 119 may further include database(s) of formatted data, including computed metric(s) for the assessment and/or raw data formatted in a data type that may be used for analysis by algorithm processor 105, modeling processor 107, and/or results processor 109. Alternately or in addition, formatted data may include calibrated data or data that meets a pre-set quality threshold for the selected visual assessment. The database(s) of formatted data may further include model data (e.g., data relating to norms/population data for a particular assessment) or interpretations of metric(s).

The user-facing frontend environment 102 provides a user with access to the assessment platform 101. User-facing environment 102 may include a web application system 113 and a web application portal 117. A user may provide eye tracking data via the web application system 113 and receive assessment results via the web application portal 117.

In one embodiment, users may take assessments via a web application system 113. The web application system 113 may be comprised of a software application installed on a device including or interfacing with an eye tracker, e.g., a Tobii® device (not shown). Physiological assessments of assessment processors 103a-103n may be displayed on a screen of the device operating web application system 113. The device may include any type of electronic device configured to send and receive data, e.g., a mobile device, smartphone, personal digital assistants ("PDA"), tablet computer, or any other kind of touchscreen-enabled device, a personal computer, a laptop, and/or server. The device may be further associated with peripheral devices, for example, button presses, joysticks, headsets, virtual reality consoles, etc. Each device may have a web browser and/or mobile browser installed for receiving and displaying electronic content received from API 119 and/or web application portal 117. The device may further include eye tracking capabilities and include wearable or remote camera(s), sensors, webcams, video cameras, remote eye trackers, mobile phones, tablet computers, spectacles, visors, helmets, implanted devices, contact lenses, or any other detection mechanisms that aid in the detection of human eyes, the location and/or orientation of the human eyes, detection of body position of the user, and/or the location and/or orientation of the wearable cameras and/or remote cameras.

The assessments may include various prompts or exercises for a user's eyes, including various visual cues for a user to look at one or more objects, etc. In one embodiment, web application system 113 may provide an interface or display comprising a listing of assessments provided by assessment processors 103a-103n. A user may select one or more assessments from the interface of web application system 113, e.g., via a "Select a Test" menu comprising a list of assessments and a checkbox next to each assessment. In one embodiment, web application system 113 may present a text describing an assessment if a user hovers a mouse, pointer, gaze, or other selection mechanism over the respective assessment. The web application system 113 may then retrieve, generate, or access a webpage and JavaScript code of the selected assessment(s) from servers of assessment platform 101 and display the assessment interface(s) to the user. The data for test selection may be pulled from API 119, which may read the data from the database. The device operating the web application system 113 may collect raw eye tracking data from the user's response to the assessment. Raw data may refer to data directly measured by an eye tracker of the device operating the web application system 113. For example, raw data may include x, y, and/or z coordinates and/or calibration data (including calibration data for the eye tracker of the device running the web application system 113 and measuring the user's eye movement).

The web application system 113 may then send the raw eye tracking data to the assessment platform 101 via the physiology evaluation API 119. Personal health information data collected through the web application system 113 may be encrypted and stored via a Health Insurance Portability and Accountability Act (HIPAA)-compliant storage platform. The web application system 113 may retrieve eye tracking data from the device via a subscriber pattern, e.g., a callback function. For example, the callback function of the web application system 113 may be invoked each time the device eye tracker captures an eye coordinate. The coordinate may then be saved with a timestamp.

In one embodiment, the web application system 113 may include or interact with a protocol buffer, e.g., protocol buffer 115. The protocol buffer 115 and/or the assessment platform 101 (e.g., API 119 or any of the various processors of the assessment platform 101) may define a data schema of physiological assessment metrics and raw eye tracking data. One benefit of providing the data schema and protocol buffer is that each metric of each assessment of the assessment processors 103a-103n may have clear definitions of each metric. For example, a metric may include measure(s) of fixations, saccades, and smooth pursuits. The data schema of the protocol buffer 115 and assessment platform 101 may provide consistent definitions on how fixation stability, saccades, smooth pursuit, dynamic visual acuity, cardinal gaze position, reaction time, reading ability, etc. are determined or measured. For instance, the data schema may dictate that a fixation may be measured as an instance where a user's eye maintains a gaze in a single location for a selected time period, e.g., at least 200 ms. The exemplary data schema may further define the minimum movement that an eye may take before it is considered not relatively stationary, and therefore performing a saccade.

The data schema further has the benefit of enforcing and clarifying the data type used for each metric, e.g., timestamps for a fixation metric and eye tracking paths for a smooth pursuit metric. The data type for each metric may further include defining which metrics to use for each assessment. For example, an autism assessment or sports training assessment may rely on smooth pursuit metrics, and an ADHD assessment may primarily use fixation and microsaccade-related metrics. Each assessment may have its own data schema, and each data schema may be set upon introducing or adding each assessment processor 103a or 103n to the assessment platform 101. Adding an assessment processor 103n to the assessment platform 101 may further include defining the metric(s) that the assessment of the assessment processor 103n may determine. For example, an ADHD assessment may help to collect raw eye tracking data that assessment platform 101 may use to compute various fixation and microsaccade-related metrics. The computed fixation and microsaccade-related metrics may then be used to evaluate a user's ADHD.

In one embodiment, assessment results may be retrieved through web application portal 117. The portal 117 may provide access to reports detailing results of the assessment(s) and provide tracking of the user's progress. Portal 117 and results processor 109 may generate all or part of such reports. In one embodiment, portal 117 may be accessed from a browser. For example, results of each assessment taken by a given user may be computed and stored at platform 101. Once a user logs into portal 117, the user may access the stored results of each assessment.

Users of the present embodiments may include any people desiring to assess and/or improve, maintain, or rehabilitate their health and wellness (e.g., in the form of detecting or diagnosing possible neurological impairment/disorder and/or evaluating or improving motor skills, cognition, and/or kinesiology. For example, users may include any individuals who perform physical activities that require observation and/or decision making ahead of physical and/or mental action. These users can include athletes, pilots, drivers, heavy machine operators, lab equipment technicians, physicians, law enforcement professionals, and/or any other individuals seeking performance enhancement or individuals involved in actions that require a cognitive process in order to respond more effectively and efficiently. Alternately or in addition, users may include individuals wanting to ensure that their vision is healthy. Alternatively or in addition, users may include learning or cognitively impaired individuals seeking to improve, maintain, or rehabilitate their mental and physical abilities. Platform 101 may be used as a diagnostics tool in a school screening context, as a home-administered consumer screening platform, as a government or local screening platform at a community facility (e.g., a pharmacy, clinic, prison, military post, etc.), as a healthcare-affiliated screening platform, etc.

Exemplary recommendations output by platform 101 may include suggesting that a user see a healthcare provider, providing a notification to a healthcare provider of a user's visual performance abilities/status (e.g., for a provider to monitor a user's disease status or progress from treatment), etc. The recommendations may include real-time reports that deliver assessment results and therapies/training based on the results. For instance, the reports may include graphical visualizations of granular and important data for a user and/or healthcare provider.

It should be appreciated that physiological assessment system 100 may include any type or combination of computing systems, e.g., handheld devices, personal computers, servers, clustered computing machines, and/or cloud computing systems. In one embodiment, physiological assessment system 100 may be an assembly of hardware, including a memory, a central processing unit ("CPU"), and/or one or more user interfaces. The memory may include any type of RAM or ROM embodied in a physical storage medium, such as magnetic storage including floppy disk, hard disk, or magnetic tape; semiconductor storage such as solid state disk (SSD) or flash memory; optical disc storage; or magneto-optical disc storage. The CPU may include one or more processors for processing data according to instructions stored in the memory. The functions of the processor may be provided by a single dedicated processor or by a plurality of processors. Moreover, the processor may include, without limitation, digital signal processor (DSP) hardware, or any other hardware capable of executing software. The one or more user interfaces may include any type or combination of input/output devices, such as a display monitor, touchpad, touchscreen, microphone, camera, keyboard, and/or mouse, or other interface.

Physiological assessment system 100 may be run over a network 121, with various components of physiological assessment system 100 running remotely or independently from one another. Alternately or in addition, physiological assessment system 100 may run locally on a device or system, e.g., without Internet access. The network may include the Internet, a content distribution network, or any other wired, wireless, and/or telephonic or local network. In one embodiment, components of platform 101 may communicate via a first network. Assessment platform 101 and user environment 102 may then communicate over a second network, different from the first network. In one embodiment, the first network and/or the second network may include a private network.

The components of the assessment platform 101 may communicate through a representational state transfer (REST) protocol. When there is an error, a log file of each system component may show where the error took place. The platform 101 may further include an automated test tool that may to test the interface between API 119, web application system 113, and web application portal 117 to ensure that data format(s) are correct. The arrangements and operations of the components (e.g., processors, devices, databases, etc.) of FIG. 1 show only one embodiment of the physiological assessment system 100. The operations may be performed by any component or arrangement of components.

Figure 2A:
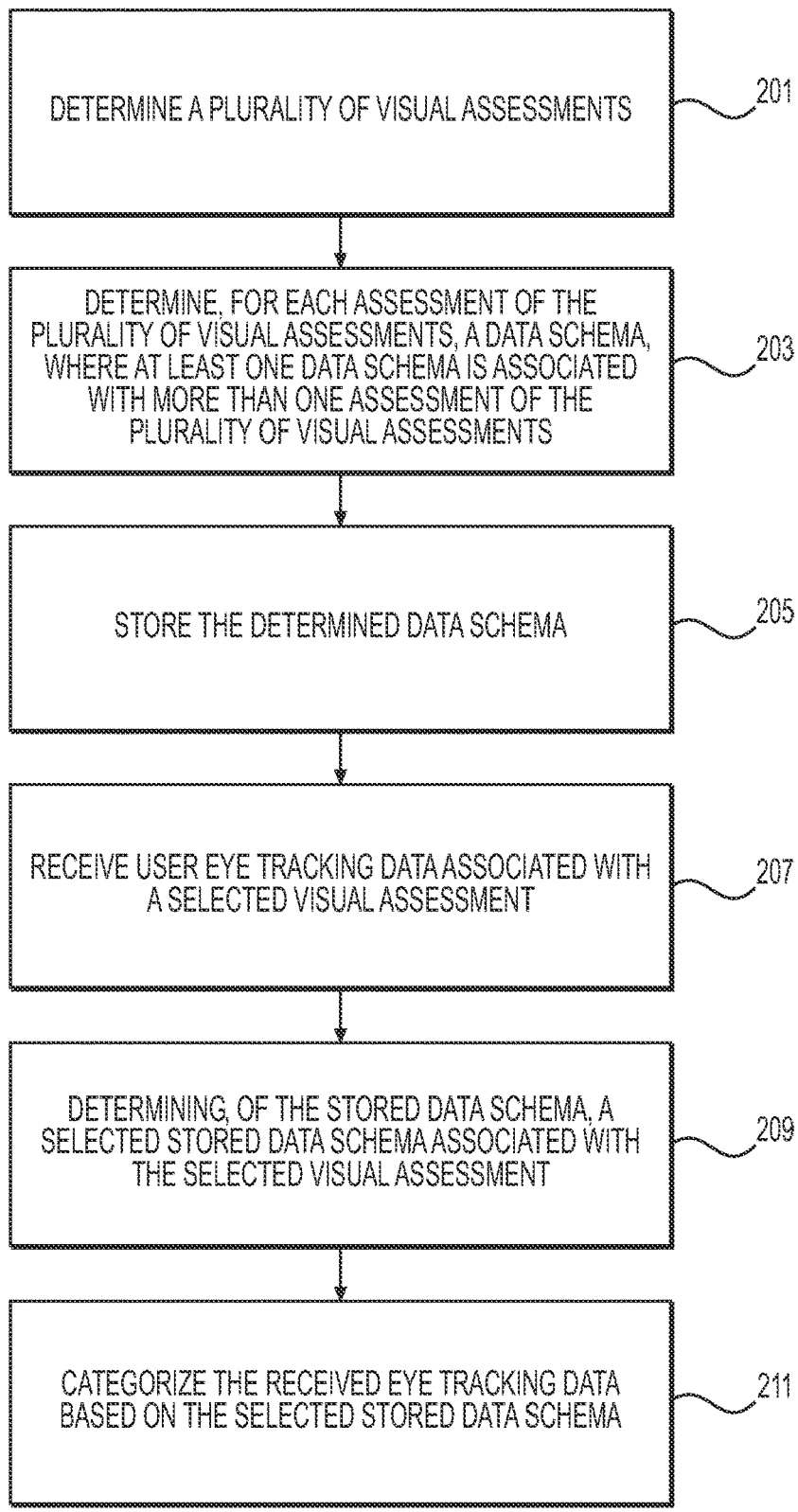
FIG. 2A is a flow diagram of an exemplary method for preparing raw eye tracking data to assess a user's physiology, according to an exemplary embodiment of the present disclosure.

FIG. 2A is a flow diagram of an exemplary method 200 for generating a data schema for a physiological assessment, according to an exemplary embodiment of the present disclosure. In one embodiment, method 200 may be performed by API 119 and/or algorithm processor 105. Step 201 may include determining a plurality of visual assessments, e.g., as offered by assessment processors 103a-103n. Step 203 may include determining, for each assessment of the plurality of visual assessments, a data schema. At least one data schema may be associated with more than one assessment of the plurality of visual assessments. In other words, step 203 may include defining a way to organize raw eye tracking data across disparate assessments. Each data schema may be associated with one or more metrics, e.g., fixation stability, saccades, smooth pursuit, dynamic visual acuity, cardinal gaze position, reaction time, reading ability. Step 203 may further include defining a data type for each metric. For example, the metric of fixation stability may be related to data types pertaining to timestamp(s) and saccades. As another example, the metric of smooth pursuit may be defined as being related to data type(s) for any data conveying a gaze path. Step 205 may include storing the determined data schema, e.g., using algorithm processor 105. Step 207 may include receiving user eye tracking data associated with a selected visual assessment of the plurality of visual assessments and step 209 may include determining, of the stored data schema, a selected stored data schema associated with the selected visual assessment. For example, steps 207 and 209 may include determining that a selected assessment evaluates a user based on a fixation(s) observed in the user's raw eye tracking data. Fixations may be the stored data schema associated with the selected assessment. Steps 207 and 209 may then involve detecting fixations in the received raw eye tracking data, e.g., detecting where the user's eye tracking data involves a gaze at a stationary location for at least 200 ms. Step 211 may include categorizing the received eye tracking data based on the selected stored data schema. Following from the previous example, step 211 may include isolating the fixations detected in the user's eye tracking data and storing the isolated fixations in the data schema of "fixations."

Figure 2B:
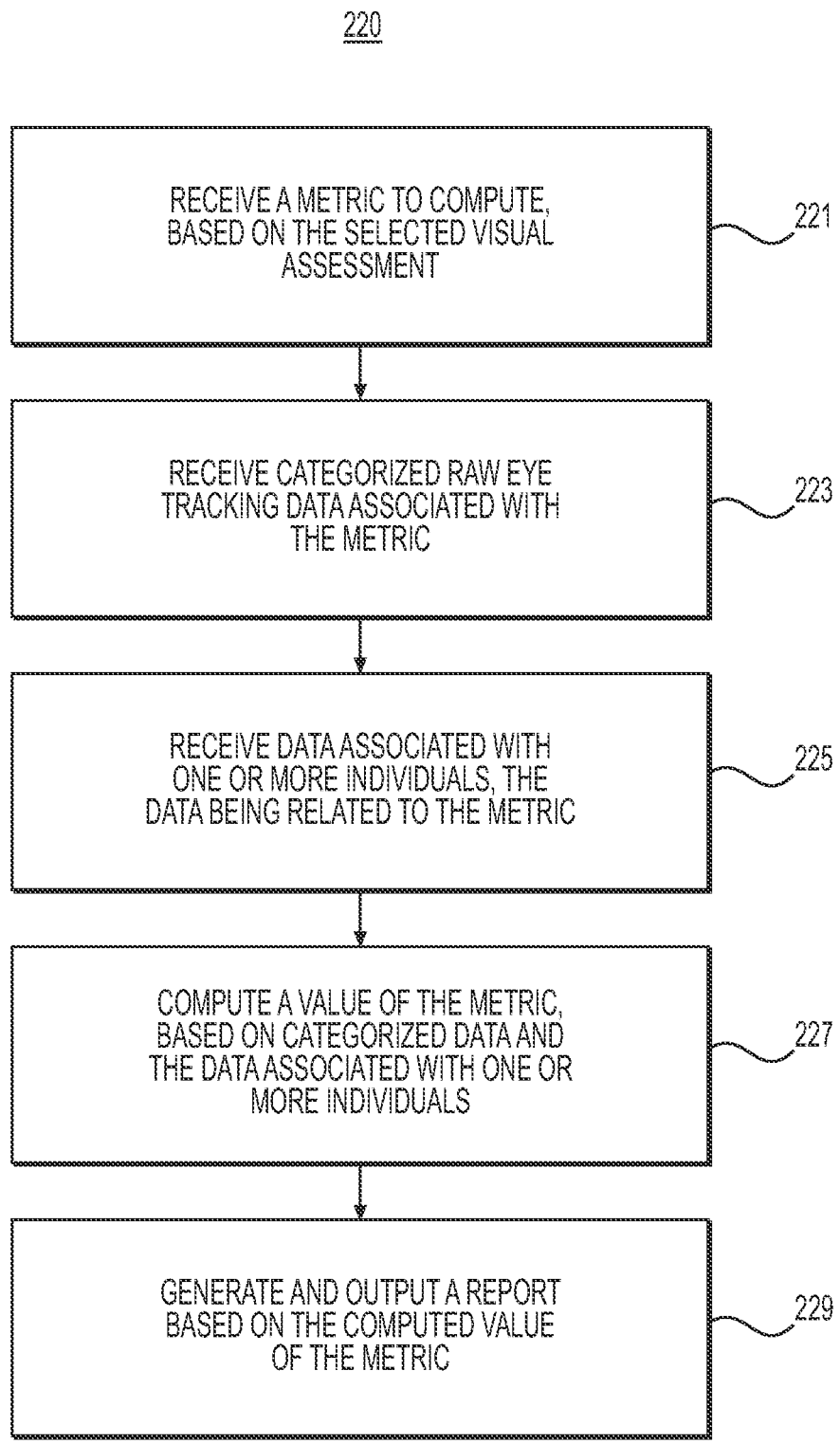
FIG. 2B is a flow diagram of an exemplary method for computing metrics for an user's physiological assessment based on processed eye tracking data, according to an exemplary embodiment of the present disclosure.

FIG. 2B is a flow diagram of an exemplary method 220 for generating a physiological assessment based on eye tracking data, according to an exemplary embodiment of the present disclosure. Method 220 may be performed by API 119, modeling processor 107, and/or results processor 109. Step 221 may include receiving a metric to compute, the metric relating to the selected visual assessment. Step 223 may include receiving categorized raw user eye tracking data (e.g., from step 211 of method 200). Step 225 may include receiving stored data relating to the metric, e.g., from modeling processor 107 and/or results database 111. The stored data may be associated one or more individuals other than the user taking the selected visual assessment or providing the raw eye tracking data. Step 227 may include computing quantitative data based on the categorized data and data related to one or more individuals other than the user. For example, step 227 may include computing a value of the metric (of step 221) based on the received categorized data of the individual and the received data associated with individual(s) other than the user. Computing the quantitative data may include filtering received user eye tracking data to remove data anomalies. The quantitative data may further be computed from an analysis of multiple metrics. For example, an ADHD assessment may be built from both saccades and smooth pursuit data. In this way, step 227 may include computing a value of a second metric of the one or more defined metrics, the second metric being different from the first metric (e.g., the metric of step 211).

Multiple metrics may also entail metrics relating to the user and another user/test subject. For example, the first metric may be based on the user eye tracking data and the second metric may be based on eye tracking data related to an individual other than the user. The quantitative data may be computed based on the computed value of the first metric and the computed value of the second metric. Population data may be generated based on the computed value of the first metric and the computed value of the second metric, where the population data relates to a test subject other than the user and the individual other than the user. In other words, population data may relate to one or more norms (or expected values for a population of users), for each metric.

Step 229 may include generating a report of user physiological function based on the computed quantitative data and/or outputting the report to a web portal (e.g., portal 117). The report may include population data, e.g., from modeling processor 107 For instance, the report may include a comparison of the user's physiological capabilities (e.g., as shown from a computed value of a metric related to the first user) to the value of the metric as given by population data. The report of physiological function may include an assessment of the user's reading performance, athletic ability, or neurological function.

In operation, physiological assessment system 100 may detect involuntary eye movement behavior to evaluate a user's physiology. A user's eye movements may be prompted through various visual displays (stimuli) on a screen. The stimuli may vary in size, speed, color, and movement for the purpose of producing the following eye movement behaviors for each eye separately and a combined (both) eye result. The observed eye movement behaviors may include saccades (e.g., fast eye movements), smooth pursuits (e.g., eye movements that follow an object), and fixations (e.g., stopping points of the eye). Exemplary physiological assessment(s) may include a reading assessment, a sports-related vision assessment, and an assessment of neurological function. Each of the assessments may provide outputs in the form of graphs, icons, charts, data tables, lists, comparisons to norms/averages, etc. The assessments may further include recommendation to improve (e.g., reading, athletic ability, or neurological function) based on the poorest results. The recommendation may include vision therapy drills. Each of the assessments may further display an indicator of the results to a specialist, e.g., an optometrist.

Exemplary Reading Assessment

The reading assessment may include a test displayed as a string, or in the form of one or more paragraphs. In one scenario, the first paragraph may appear automatically. When the user presses a button, the current paragraph may be hidden, words per minute may be calculated and recorded, and the next paragraph may be shown. If there is no additional paragraph to show, the reading portion of the assessment may end. The word count and timing of the user's reading (as determined from collected eye tracking data) may be processed for a words per minute (wpm) calculation. One embodiment may include prompting or entering an initial reading level for the assessment, and appropriate content may be shown. After text is read, questions may be answered to gauge comprehension. Different stimuli (e.g., numbers) may be shown to people who have trouble reading for any number of reasons.

The reading assessment may be provided in various languages or difficulty levels. Analysis of eye tracking data may be based on the following factors:

Grade level of the text presented by the reading assessment;

Lines to analyze in the presented text (e.g., the total number of lines);

Lines found by the user (e.g., lines read or found by the user's gaze);

Lines found by analysis (e.g., return sweeps of a user's gaze per page of text);

Age of the user at the time of testing;

Title of the text read;

Head movement percentage, e.g., the percentage of the movement done with head versus eyes;

Vergence;

Recording Time, e.g., the amount of time useful data was recorded. Recording time may influence analysis reliability;

Analysis Reliability, e.g., the level of confidence in the report metrics and outcome (where n analysis reliability score lower than 80% may cause the system 100 to prompt the user to retake the assessment;

Dry Eye, e.g., whether the user has clinically determined dry eyes;

Visual Fatigue, e.g., the tiredness of the user's eyes;

Binocular Vision Issues, e.g., whether the eyes travel in similar patterns;

Fixations/100 Words (#), e.g., a stopping point of the eyes;

Regressions/100 words (#), e.g., the number of times the user looked backwards (in English content this is from right to left), while reading;

Average Fixation Duration (ms), e.g., the average amount of time the reader stopped (fixated) while reading;

Reading Rate (words/minute; #), e.g., how many words were read per minute of reading;

Regression/Fixation Ration (%);

Correct Comprehension Answers (%), e.g., the number of comprehension questions were answered correctly; and Disparity Between Eyes (mm), e.g., the difference between the left and right eye taken at fixations then divided by the number of fixations.

Exemplary Sports-Related Vision and Training Assessment

The Sports-Related Vision and Training Assessment may include various areas of vision that impact a user's athletic performance. The assessment may be built from four types of metrics: functional, mechanics, mind-eye, and on-field. Functional metrics may refer to the ability to have basic, fundamental visual health and functionality such as acuity, contrast, dryness. Mechanics may refer to the ability of the eyes to work together, the muscle and nerve coordination to maintain effective and efficient use of the eyes, etc. Mind-Eye may refer to the interplay of vision and neuro-connectivity to include visual processing. On-Field may refer to how environmental factors can influence performance including vision via motor responses such as reactions, impulses and distractibility. The four types of metrics may be inter-dependent. For instance, having poor functional skills may also affect a user's mechanics, mind-eye ability, or on-filed ability.

Percentiles may be given for each type of metric as the overall weighted percentile. Percentiles may show where a given user stands compared to their peers. For example, a score output by the assessment at 50th percentile may mean that the user scored better than 50 out of every 100 athletes at the user's designated skill level. The assessment output may include may include a weighted score developed by optometrists, coaches, and sport vision experts. This score may be based on athletic performance needs.

Norms for sports-related assessment data may be calculated across various categories, e.g., Elite, Professional, College, Elite Youth, Amateur, etc. The sports-related assessment may generate values for the following metrics or types of eye movements: Circular Smooth Pursuit (CSP), Horizontal Smooth Pursuit (HSP), Vertical Smooth Pursuit (VSP), Horizontal Saccades (HS), Vertical Saccades (VS), Fixation Stability, Choice Reaction Time (CRT), Discriminate Reaction Time (DRT), Contrast, Static Visual Acuity (SVA), Dynamic Visual Acuity (DVA), etc. The sports-related assessment may further evaluate a user based on the following factors.

Static (Visual) Acuity, e.g., the ability to see stationary objects clearly (20/20), such as reading a play book;

Dynamic (Visual) Acuity, e.g., the ability to see moving objects (object size fixed) clearly, such as tracking a ball or reading hand signals;

Dry Eye, which can affect visual clarity and fatigue;

Fixation Stability, e.g., the ability to keep the eyes stable and fixed on a certain spot for a period of seconds;

Fatigue, e.g., visual fatigue or tiredness of the eyes which can affect many aspects of visual performance;

Mechanics, e.g., coordination between each eye, as well as muscle and nerve coordination to maintain effective and efficient use of the eyes;

Latency, e.g., the amount of time it takes the eyes to react when a target is presented;

Targeting, e.g., the accuracy between the target and where a user's eye gazes;

Speed, e.g., the velocity of a user's eyes;

Binocular Vision Issue, e.g., a measure of the extent to which a user's eyes are "teaming" or working in unison or in coordination with each other;

Mind-Eye metric(s), e.g., interplay of vision and neuro-connectivity to include visual processing, including, e.g., processing time (e.g., the time it takes to "think" once something is seen), decision making accuracy (e.g., the outcome of the thought and whether a user's response is correct or incorrect, reaction time (e.g., how quickly a user responded to the task;

On-Field metric(s), e.g., how environmental factors can influence performance including vision via motor responses, including, e.g., distractibility (e.g., a user's ability to pay attention to the task or assessment at hand), impulsivity (e.g., a user's ability to be "patient," waiting for the information to present itself before responding, etc.

The assessment may also be based on the following factors:

Contrast Sensitivity, which may measure visual function, for instance, in situations of low light, fog, glare, or in the sun). One scenario may include when the contrast between, for example the white ball and the grey clouds is reduced. A low ability in contrast may affect a players' performance on cloudy days or in night games.

Depth, which may include a measure of the point at which the eyes converge compared to a point of focus. A negative number may mean the point of convergence is further than the required focus point. A positive score may mean the point of convergence is closer than the required focus point.

Tracking ability, which may measure the ability of both eyes working in coordination to follow an object, such as a ball. One way of expressing tracking ability may include a Smooth Pursuit Percentage in response to the assessment.

Disparity, which may measure the difference between each eye when looking at a target. Disparity may include a measure of whether a user's eyes focus together, allowing the user to see clearly or whether the user's eyes focus apart, affecting their depth perception.

Efficiency, which may measure the path a user's eyes take from one target to the other. Like running bases in baseball, efficiency measures whether a user's eyes take the most efficient/shortest/most direct pathway to view a target, or engage in extra motions that increase the time it takes for the gaze to reach the next visual target of the assessment.

Speed (/Accuracy Trade-off) may refer to the trade-off that occurs between a user moving their eyes quickly, while also being fast. Depending on the sport, a user may need one more than the other, or both equally.

Exemplary Assessment of Neurological Function

The assessment of neurological function may evaluate brain health and function as reflected in oculomotor behavior. The assessment may include various measured aspects of vision, including oculo-motor function in each eye (eye muscle function (e.g., overactive or underactive for each eye), fixations, pursuits, and saccades. The assessment may further include: determining linkage(s) between the measured aspects of vision to brain function (or dysfunction), determining typical symptom(s) that are experienced in a person (where an area of brain dysfunction is identified), determining typical risk(s) that are associated with a person's life (with the area of brain dysfunction identified), recommending specifically-targeted therapy to improve in the area of the identified area of brain dysfunction, etc.

Exemplary Outcome categories may include the following: Normal (e.g., no indication of brain health issues based on reference model data), Not normal (e.g., indication of abnormal behavior that is indicative of some brain related issue based on a reference brain health model, which may be different from other issues such as dry eye), Level of Normality (e.g., the statistical probability of a persons' level of normal to not normal), etc. Additional categories include diagnoses or evaluations of concussion, multiple sclerosis, diabetes, dementia, and/or other visual and/or brain related processes.

Analytics Processes may include data collection, cleaning, transformation, formatting, clinical verification, modelling features, profiling, comparing profiles, providing results. Exemplary data modeling and analytical models of the neurological function assessment may be created using various analytical processes and/or algorithms such as logistical regression, information criterion, Gaussian Finite Method, Boolean approaches, principle component analysis, Cox Model, Gradient Boosting model. Additional analysis may include confidence intervals, probabilities, ROC curves, Random Forest, sensitivity, specificity, precision, accuracy. Additional and ongoing monitoring and analytics may include machine learning and may be programmed to mine data, make projections, and determine relationships. The analytics process may be derived from the following:

Score (provided in different units, e.g., millimeters, degrees etc.) may include a user's score on a metric.

Percentiles may show where a user stands compared to others users/individuals. 50th percentile may mean a user scored better than 50 out of every 100 people. For some assessments, a high percentile may indicate brain health.

Smooth Pursuit Percentage may refer to eye movements that follow a target/visual cue within a velocity range of the target/visual cue. The eye movements may be reported as a percentage of the test time. For some assessments, a high smooth pursuit measurement may indicate brain health.

Efficiency (measured in millimeters) may refer to the error in a user's' gaze, relative to a reference or ideal pathway (that is the pathway the stimuli takes during testing). For some assessments, a low efficiency measurement may indicate brain health.

Variability (measured in millimeters) may refer to the average variance of a user's response to an assessment, from a reference or ideal pathway. Observed or received user data may include (or be evaluated to include) variance in three segments of the pathway, middle, left/right or up/down.

Eccentric variability may refer to the variability in a user's assessment response, on the left and right portions of the screen that are outside central gaze position.

Recovery (measured in millimeters) may refer to the difference in a user's visual path taken before and after a fixation. A wide, looping path may be inefficient. A narrow path, where the eye moves without great loops, may be preferred. For some assessments, a low recovery measurement may indicate brain health.

Target Accuracy (measured in millimeters) may refer to a distance from a target, including the distance each "hit" or fixation location was, compared to the ideal target location at a given time. For some assessments, a low target accuracy measurement may indicate brain health.

Speed may refer to the average velocity of a user's saccades across the duration of an assessment. For some assessments, a higher speed measurement may indicate brain health.

Pathway Length Differences (measured in millimeters) may refer to the average difference in distance between an eye gaze pathway of the right versus an eye gaze pathway of the left eye. For some assessments, a low pathway length difference may indicate brain health.

Distance (measured in millimeters) may refer to the average distance a user's gaze pathway is from an ideal or reference pathway. For some assessments, a low distance measurement may indicate brain health.

Depth (measured in millimeters) may refer to the difference between a point of convergence of a user's eyes and the screen, as provided by an eye tracker. A negative number may indicate a point of convergence behind the screen. A positive number may indicate a point of convergence in front of the screen.

Phoria may refer to deviation of the line of sight inward (eso+) or outward (exo−). A user displaying no deviation (ortho) (e.g., a result of zero) may have good brain health.

Tropia may refer to deviation of a user's line of sight, where one eye may be above the other. If the tropia value is a negative value, the user's left eye may be higher than the right. If the tropia value is positive value, then the user's right eye may be higher than left. A tropia value close to zero may be preferred.

Other data related to amplitude, velocity, convergence, head movement, gaze spread, object recognition, gaze pathways, efficiency, variability, size, and others. Additional eye tracking metrics may incorporate fixations, saccades, smooth pursuits, square wave jerks, glissades, microsaccades and others. Raw data may also be used to analyze trends, develop additional metrics.

The assessment may include training and/or therapy recommendations. The training or therapy may be linked to deficiencies and recommended as treatment to improve abnormalities. Various graphs may be used in reports to display metrics. Graphs may include line graphs, bar charts, pie charts for example. Alternately or in addition, reports may include visualizations, e.g., gaze replays, real time analytical display of results and other visualizations. The report may include an exemplary proprietary scale of Functional Status, providing analysis ranging from a broad interpretation of received data to a specific analysis. For example, a report may include the "scale of functional status." This scale may provide a range of performance that goes from dysfunctional to functional to exceptional performance. In other words, the scale may provide a level of normality or functional status across all the eye movement classifications and metrics. A user may then drill down into segments of the report for more detail on each metric and how it relates to neurological performance.

One exemplary scale of functional status of the report ranges from zero to 100. Zero may represent complete dysfunction. 100 may represent exceptionally good performance. "Functional performance," which may lie between dysfunctional and exceptional performance may show the average performance across a population. A user and doctor may determine where the user falls on the scale. For example, if a user is a professional athlete looking to gain an edge, "functional performance" may not be sufficient. The professional athlete user may strive to attain exceptional performance. On the other hand, if a user is an elderly person who is looking to determine if s/he can still drive, "functional performance" may be a sufficient level of performance.

The scale may be visualized in a report with changes in color from red to orange to yellow to green. In one embodiment, red may indicate dysfunctional performance and green may indicate performance in the functional and exceptional range. Ranges of "functional" may be adjusted in accordance with a user's age. In other words, the very young and very old may have wider functional ranges than the middle aged. In one embodiment, the functional range for a specific sport level or special group can be calculated and reported for a customized range.

In one embodiment, report(s) may further include data related to right and left eyes with the oculo-motor muscles. The oculo-motor muscles may work to push and pull the eyes in different ways. If there is an imbalance in these muscles, where one muscle is overactive, and/or another muscle is underactive, pursuit tracking may be affected. The irregularity in the pursuit tasks may be displayed in eye tracking data when odd shapes or patterns occur. The assessment of neurological function may measure these patterns in the vertical and horizontal smooth pursuit tasks. The assessment may also identify, for example, "V"-shaped patterns, "A"-shaped patterns, "X"-shaped patterns, diamond patterns, or rare patters in both or one eye. Once such a pattern is identified, the assessment may show the likely muscles (e.g., in red color), affected by such a pattern. The muscles may be labeled under the image. Furthermore, a description of the pattern as well as possible symptoms and risks may be displayed. The muscle imbalance may be linked to a training module for specific rebalancing therapy.

The report may further include a stack of blocks that categorize one or more major eye movements, fixations, pursuits, saccades, etc. A fixation may provide a stopping point of the eye and form the base of vision and visual stability. Pursuits may include eye movements that follow a target, e.g., a ball or moving car. Saccades may include fast eye movements that are designed to relocate our focal vision to an area within the vision field. Each block may include the labels, "My Score" and "percentile." "My score" may refer to a weighted score the user attained from the metrics within that category. A weight may include the contribution that metric made toward the overall score. The weight may be developed through analytics that look to differentiate functional from dysfunctional vision. The score may be compared to an overall database including scores for people across the spectrum of age, gender, ethnicity etc. The comparison may provide a percentile. A percentile of 80 may indicate that the user received a score higher than 80 out 100 people in the database. A percentile score of 20 may indicate that a user received a score got higher than 20 out of 100 people in the database. A higher percentile may be preferred, as the higher percentage may indicate a higher functional status.

Based on a user's percentile, each major classification, e.g., fixations, saccades, and pursuits, may be given a color. If a user's percentile is low, the user may be given a red color for that eye classification. For example, if the user's fixation percentile was 10, the fixation block in the user's report may be colored red. If the user's fixations were in the 90th percentile, the user's fixation block may be colored green. As there are more pursuit metrics and those metrics may have more weight than saccades metrics, and more saccade metrics that have more weight than fixation metrics, each block may contribute on a different level to a user's overall score. The metrics may be weighted differently based on the neurological function assessment analytics model, that is they may contribute at different rates compared to each other when determining if a user's eye movements overall are functional or dysfunctional.

The report may include an image of the brain, based on which area shows the greatest dysfunction and has the highest weight. If a user's area of greatest dysfunction is fixations, then the major brain area affected may be displayed in the report as the brain stem. If a user's area of greatest dysfunction is pursuits, then the major brain areas affected may be displayed in the report as the parietal lobe and cerebellum. If a user's area of greatest dysfunction is saccades, then the major brain areas affected may be displayed in the report as the frontal lobe and cerebellum.

The colors of each block may be determined in an exemplary embodiment as follows: If a user has two blocks that are red, e.g., saccades and pursuits, the report may show the brain region(s) related to pursuits as those contribute more to one's overall health and function. A training module associated with the neurological function assessment may show exercises linked to a user's greatest deficiencies first. The report may include written content below the images of the brain. This written content may include a description of what major eye movement was most dysfunctional, and how the movement is defined. The written content may further include typical symptoms and risks associated with this dysfunction. In one embodiment, the training exercises may be provided with the written content. The training test(s) may link a user's highest dysfunction to a therapy exercise that can help the user improve their performance.

The report may include vertical tests, including vertical tracking or pursuits and vertical speed and targeting or saccades. The report may include a ledger at the bottom of the page indicating what various the acronyms mean e.g., "SP"=smooth pursuit. The second page of the report may include definitions of all the metrics on the report. The report may include an image of the user facing forward show the perspective of a gaze replay. When online, the user may press play to see any of these gaze patterns in motion. The left and in the bottom corner of the report may include horizontal speed and targeting or saccades, the report may also include the horizontal tracking which is related to pursuits, and then stability which is related to fixations. The report may further include, at the top, a display indicating circular smooth pursuit. Each of this test data may be presented in any variety of orders or configurations. The above description includes only one exemplary format for the report.

The platform 101 may perform the following exemplary assessment steps for eye muscles. First, trends in pattern tracing may be hundreds of different data sets, e.g., using modeling processor 107 of platform 101. The data sets may be compared to known clinical outcomes to determine a level of match or correspondence. Mathematical equations may be created that capture the patterns that are matched with clinical outcomes. A level of accuracy may be determined between the mathematical equations and the verified clinical results until a minimum predetermined accuracy threshold is acquired. The level of severity of a user's deviation from the level of accuracy may be determined based on thresholding. (Numbers from a model/normal/expected data set may be used for the computation of the level of severity.) The platform may further link dysfunction (given by the level of severity) to muscles. For a report, the severity may be linked to a color code, e.g., to provide a color-coded visualization/display by the severity of dysfunction.

The platform 101 may perform the following exemplary assessment steps for brain regions. For example, brain regions may be categorized into various eye movement categories (e.g., fixations, saccades, and pursuits). Platform 101 (e.g., modeling processor 107) may The platform 101 may compare received user eye tracking data sets to known clinical outcomes to determine a level of match. Platform 101 may further create mathematical equations that capture the patterns that are matched with clinical outcomes. A level of accuracy between the mathematical equations and the verified clinical results may be determined until a minimum predetermined accuracy threshold is acquired. A logistical regression may be conducted to determine weighted contributions of the metrics and overall weights may be calculated for each major eye classification (e.g., fixation, saccade, pursuit). The platform 101 may also determine the probability of normality (dysfunctional, functional, and exceptional) for each individual, compared to the model population data set. The platform 101 may further determine the level of dysfunction for each eye classification (e.g., fixation, saccade, pursuit, etc.), link dysfunction to brain image, and for the purposes of the report, link severity to color, e.g., to produce a color-coded visualization of the severity of dysfunction. The platform 101 may further link content of symptoms and risks based on the greatest eye movement classification dysfunction and generate a detailed description of exemplary measured aspects of vision and possible linkage(s) between the measured aspects of vision to brain function/dysfunction.

In summary, the disclosed systems and methods provide a range of formerly silo-ed and disparate assessments and training options at a single source. To do so, the disclosed systems and methods recognize that eye tracking data may provide visual assessments, skill optimization, and medical diagnostic testing and treatment. The disclosed systems and methods therefore enable communication between various physiological assessment applications that generate and collect user eye-tracking data. Although the assessments relate to different functions, the disclosed systems and methods provide a platform that can compute outcomes for each of the different functions, using the common base of eye tracking data.

Other embodiments of the disclosure will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. A computer-implemented method of assessing a user physiology and performance, the method comprising:
   determining, via at least one processor, a plurality of visual assessments, each visual assessment comprising an eye tracking exercise applicable to evaluate at least one of a plurality of physiological functions of the user, wherein the plurality of physiological functions are across a plurality of categories including reading ability, physical performance vision, and neurological function;
   receiving, via the at least one processor, user eye tracking data associated with the user's performance of the physiological function corresponding to a selected visual assessment of the plurality of visual assessments;
   determining and accessing, via the at least one processor, a stored data schema corresponding to the selected visual assessment;
   categorizing, by the at least one processor, the received eye tracking data based on the determined and accessed stored data schema;
   retrieving, by the at least one processor, categorized eye tracking data related to one or more individuals, the categorized eye tracking data being categorized based on the stored data schema;
   computing, by the at least one processor, quantitative data based on the categorized user eye tracking data and the retrieved categorized eye tracking data related to one or more individuals; and
   generating and displaying, by the at least one processor, an electronic interface comprising an evaluation of the physiological function of the user, corresponding to the selected visual assessment, based on the computed quantitative data.

2. The method of claim 1, further comprising:
   determining one or more metrics for the stored data schema; and
   determining a data type for each metric of the one or more metrics.

3. The method of claim 2, further comprising:
   filtering the user eye tracking data to remove data anomalies; and
   generating a value of a first metric of the one or more metrics based on the filtered user eye tracking data, wherein the quantitative data includes the first metric.

4. The method of claim 3, further comprising:
   generating a value of a second metric of the one or more metrics, the second metric being unequal to the first metric; and
   computing the quantitative data based on the value of the first metric and the value of the second metric.

5. The method of claim 4, wherein the value of the first metric is based on the user eye tracking data, and wherein the value of the second metric is based on eye tracking data related to an individual other than the user.

6. The method of claim 5, further comprising:
   generating a set of population data based on the value of the first metric and the value of the second metric, wherein the set of population data is associated with a test subject other than the user and the individual other than the user.

7. The method of claim 6, further comprising:
   generating the electronic interface comprising the evaluation based on a comparison of the value of the first metric and the generated set of population data.

8. The method of claim 1, wherein the evaluation includes an assessment of a reading performance, athletic ability, or neurological function of the user.

9. A system for assessing a user physiology and performance, the system comprising:
   a data storage device storing instructions for hosting one or more visual assessments; and
   a processor configured to execute the instructions to perform a method comprising:
      determining, via at least one processor, a plurality of visual assessments, each visual assessment comprising an eye tracking exercise applicable to evaluate at least one of a plurality of physiological functions of the user, wherein the plurality of physiological functions are across a plurality of categories including reading ability, physical performance vision, and neurological function;
      receiving, via the at least one processor, user eye tracking data associated with the user's performance of the physiological function corresponding to a selected visual assessment of the plurality of visual assessments;
      determining and accessing, via the at least one processor, a stored data schema corresponding to the selected visual assessment;
      categorizing, by the at least one processor, the received eye tracking data based on the determined and accessed stored data schema;
      retrieving, by the at least one processor, categorized eye tracking data related to one or more individuals, the categorized eye tracking data being categorized based on the stored data schema;
      computing, by the at least one processor, quantitative data based on the categorized user eye tracking data and the retrieved categorized eye tracking data related to one or more individuals; and
      generating and displaying, by the at least one processor, an electronic interface comprising an evaluation of the physiological function of the user, corresponding to the selected visual assessment, based on the computed quantitative data.

10. The system of claim 9, wherein the processor is further configured to:
    determine one or more metrics for the stored data schema; and
    determine a data type for each metric of the one or more metrics.

11. The system of claim 10, wherein the processor is further configured to:
    filter the user eye tracking data to remove data anomalies; and
    generate a value of a first metric of the one or more metrics based on the filtered user eye tracking data, wherein the quantitative data includes the first metric.

12. The system of claim 11, wherein the processor is further configured to:
    generate a value of a second metric of the one or more metrics, the second metric being unequal to the first metric; and
    compute the quantitative data based on the value of the first metric and the value of the second metric.

13. The system of claim 12, wherein the value of the first metric is based on the user eye tracking data, and wherein the value of the second metric is based on eye tracking data related to an individual other than the user.

14. The system of claim 13, wherein the processor is further configured to:
generate a set of population data based on the value of the first metric and the value of the second metric, wherein the set of population data is associated with a test subject other than the user and the individual other than the user.

15. The system of claim 14, wherein the processor is further configured to:
generate the electronic interface comprising the evaluation based on a comparison of the value of the first metric and the generated set of population data.

16. The system of claim 9, wherein the evaluation includes an assessment of a reading performance, athletic ability, or neurological function of the user.

17. A non-transitory computer-readable medium storing instructions that, when executed by a computer, cause the computer to perform a method of assessing a user physiology and performance, the method comprising:
determining, via at least one processor, a plurality of visual assessments, each visual assessment comprising an eye tracking exercise applicable to evaluate at least one of a plurality of physiological functions of the user, wherein the plurality of physiological functions are across a plurality of categories including reading ability, physical performance vision, and neurological function;
receiving, via the at least one processor, user eye tracking data associated with the user's performance of the physiological function corresponding to a selected visual assessment of the plurality of visual assessments;
determining and accessing, via the at least one processor, a stored data schema corresponding to the selected visual assessment;
categorizing, by the at least one processor, the received eye tracking data based on the determined and accessed stored data schema;
retrieving, by the at least one processor, categorized eye tracking data related to one or more individuals, the categorized eye tracking data being categorized based on the stored data schema;
computing, by the at least one processor, quantitative data based on the categorized user eye tracking data and the retrieved categorized eye tracking data related to one or more individuals; and
generating and displaying, by the at least one processor, an electronic interface comprising an evaluation of the physiological function of the user, corresponding to the selected visual assessment, based on the computed quantitative data.

18. The non-transitory computer-readable medium storing instructions of claim 17, the method further comprising:
determining one or more metrics for the data schema; and
determining a data type for each metric of the one or more metrics.

19. The non-transitory computer-readable medium storing instructions of claim 18, the method further comprising:
filtering the user eye tracking data to remove data anomalies; and
generating a value of a first metric of the one or more metrics based on the filtered user eye tracking data, wherein the quantitative data includes the first metric.

20. The non-transitory computer-readable medium storing instructions of claim 19, the method further comprising:
generating a value of a second metric of the one or more metrics, the second metric being unequal to the first metric; and
computing the quantitative data based on the value of the first metric and the value of the second metric.

* * * * *